United States Patent
Billard

(10) Patent No.: US 10,435,484 B2
(45) Date of Patent: Oct. 8, 2019

(54) INACTIVATION OF OFF-TASTE INDUCING ENZYMES

(71) Applicant: DUPONT NUTRITION BIOSCIENCES APS, Copenhagen (DK)

(72) Inventor: Lionel Billard, Celles sur Belle (FR)

(73) Assignee: DUPONT NUTRITION BIOSCIENCES APS (DK)

(*) Notice: Subject to any disclaimer, the term of this patent is extended or adjusted under 35 U.S.C. 154(b) by 0 days.

(21) Appl. No.: 15/388,073

(22) Filed: Dec. 22, 2016

(65) Prior Publication Data

US 2017/0233500 A1 Aug. 17, 2017

Related U.S. Application Data

(62) Division of application No. 13/513,126, filed as application No. PCT/EP2010/069295 on Dec. 9, 2010, now abandoned.

(30) Foreign Application Priority Data

Dec. 10, 2009 (EP) .................................. 09178663

(51) Int. Cl.
| | | |
|---|---|---|
| C08B 37/00 | (2006.01) | |
| C12N 9/99 | (2006.01) | |
| A23L 29/269 | (2016.01) | |
| A61K 47/36 | (2006.01) | |

(52) U.S. Cl.
CPC .......... *C08B 37/006* (2013.01); *A23L 29/272* (2016.08); *A61K 47/36* (2013.01); *C12N 9/99* (2013.01); *C12Y 301/06001* (2013.01); *C12Y 302/01017* (2013.01); *C12Y 302/01031* (2013.01); *C12Y 304/21062* (2013.01); *A23V 2002/00* (2013.01)

(58) Field of Classification Search
CPC .......... C08B 37/00; A61K 47/36; C12N 9/99; A23L 29/269
See application file for complete search history.

(56) References Cited

U.S. PATENT DOCUMENTS

| | | |
|---|---|---|
| 6,663,911 B2 | 12/2003 | Valli et al. |
| 7,361,754 B2 | 4/2008 | Cleary et al. |
| 8,231,921 B2 | 7/2012 | Bezanson et al. |
| 2005/0266138 A1 | 12/2005 | Yuan et al. |
| 2006/0003051 A1 | 1/2006 | Cleary et al. |
| 2008/0145505 A1* | 6/2008 | Bezanson ............ A23G 3/42 426/576 |

FOREIGN PATENT DOCUMENTS

| | | |
|---|---|---|
| WO | 2002/060268 A2 | 8/2002 |
| WO | 2006/009938 A2 | 1/2006 |
| WO | 2008/076719 A2 | 6/2008 |

OTHER PUBLICATIONS

Kawabata et al. Specific IgE and IgG1 responses to subtilisin Carlsberg (alcalase) in mice: development of an intratracheal exposure model. Fundam Appl Toxicol. 1996;29(2):238-43.*
PCT International Search Report for Application No. PCT/EP2010/069295; Lejeune, Robert, Authorized Officer; ISA/EPO; dated May 11, 2011.
Morris, "Bacterial Polysaccharides" Chapter 11 in Food Polysaccharides and Their Applications, 1995, pp. 341-375, Editor Alistair M. Stephen, Marcel Dekker, Inc. (Book Not Included).
Miyazaki et al., "In situ-gelling gellan formulations as vehicles for oral drug delivery," Journal of Controlled Release, 1999, vol. 60, pp. 287-295.
Kim et al., "Purification and characterization of arylsulfatase from *Sphingomonas* sp. AS6330," Appl. Microbiol. Biotechnol. 2004, vol. 63, pp. 553-559.
Kawabata et al., "Specific IgE and IgG1 Responses to Subtilisin Carlsberg (Alcalase) in Mice: Development of an Intratracheal Exposure Model," Fundamental and Applied Toxicology, 1996, vol. 29, No. 27, pp. 238-243.
Giavasis et al., "Gellan Gum," Critical Reviews in Biotechnology, 2000, vol. 20, No. 3, pp. 177-211 (Abstract).
Duxbury, "Multi-functional gum gets final FDA approval," Food Processing Magazine, Feb. 1993, pp. 62.

\* cited by examiner

*Primary Examiner* — Lynn Y Fan

(57) ABSTRACT

The present inventions relates to a method for the production of gellan gum, under mixing conditions, the method comprising a) providing a fermentation broth or other liquid medium containing gellan gum, b) if necessary adjusting the temperature and the pH of the fermentation broth/liquid medium to allow or facilitate enzymatic treatment in step c, c) adding one or more enzymes capable of reducing or abolishing the enzymatic activity of *S. elodea* derived arylsulfatase and/or β-glucuronidase, said one or more enzymes being added in an amount sufficient to reduce or abolish the enzymatic activity of *S. elodea* derived arylsulfatase and/or β-glucuronidase in the broth/liquid medium, and/or treating the broth/liquid medium at a temperature between 90° C. and 125° C. for a period of time sufficient to reduce or abolish the enzymatic activity of *S. elodea* derived arylsulfatase and/or β-glucuronidase in the broth/liquid medium, and d) optionally recovering the gellan gum from the gellan gum containing broth/liquid medium.

10 Claims, No Drawings

INACTIVATION OF OFF-TASTE INDUCING ENZYMES

CROSS-REFERENCE TO RELATED PATENT APPLICATIONS

This specification claims priority as a continuation under 35 USC § 120 to U.S. patent application Ser. No. 13/513,126 (filed May 31, 2012; published on Sep. 20, 2012 as US Patent Publ. No. US2012/0238643), which, in turn, claims priority under 35 USC § 371 as a national phase of Int'l Patent Appl. PCT/EP2010/069295 (filed Dec. 9, 2010; and published on Jun. 16, 2011 as Int'l Publ. No. WO2011/070119), which, in turn, claims priority to European Patent Appl. No. 09178663.2 (filed Dec. 10, 2009). The entire texts of the above-referenced patent applications are incorporated by reference into this patent.

FIELD OF THE INVENTION

The present invention relates to reduction of problems with off-taste derived from the activity of impurities in food containing gellan gum. In particular, the present invention relates to means and methods for reducing paracresol formation in gellan containing food products.

BACKGROUND OF THE INVENTION

Gellan gum is a water-soluble polysaccharide produced by the bacterium *Sphingomonas paucimobilis* formerly named as *Sphingomonas elodea* or *Auromonas elodea* or *Pseudomonas elodea* (Pollock, 1993).

High acyl (HA) Gellan gum is used primarily as a gelling agent. It is able to withstand 120° C. heat. As a food additive, gellan gum is used as a thickener, emulsifier, and stabilizer. If the gellan gum is added, subsequently heated and cooled, the gellan gum provides a gel of unique structure. In manufacture of various dairy products the gellan gum acts as a stabilizer to help formation of a gel. The gellan gum's heat stability and low viscosity at high temperature are especially useful in manufacturing a product going through heat treatment, such as ultra high temperature (UHT) or high temperature short time (HTST) treatments.

In foods, gellan gum is used in a variety of products, cf. Duxbury, D D: "Multi-functional gum gets final FDA approval: gellan gum offers formulators low use levels and high versatility", Food Processing. Issue February 1993. Typical food products incorporating gellan gum include bakery fillings, confections, dairy products, dessert gels, frostings, icings and glazes, jams and jellies, low-fat spreads, microwavable foods, puddings, sauces, structured foods, and toppings. Gellan gum also may be used in canned cat and dog food.

In pharmaceutical products gellan gum can be used to produce easy-to-swallow solid dosage forms, such as gels and coated tablets, and to modify the rate of release of active ingredients from tablets and capsules.

However, when adding gellan gum it is almost inevitable that the end product is also contaminated with enzymes derived from the bacterial fermentation production of the gum, since the gellan gum is typically used in a relatively impure form. These residual enzymes (described as β-glucuronidase and arylsulphatase) are in turn responsible for development of an undesirable off-taste in the end-product (often described as a barn-like or cow-like taste): over time para-cresol (p-cresol) forms as a result of the action of enzymes produced by *S. paucimobilis*.

Several solutions to this problem have been suggested previously.

In US patent application publication 2006/0003051, it is suggested to produce a gellan gum composition by a fermentation process comprising growing *Sphingomonas elodea* in a culture medium, wherein the *Sphingomonas elodea* produces no catalytically active arylsulfatase or no catalytically active β-glucuronidase or no catalytically active arylsulfatase and no catalytically active β-glucuronidase. In other words, US 2006/0003051 utilises genetically modified *S. elodea*, where the genes encoding the two enzymes are suppressed or silenced.

It has also been suggested to pretreat the raw gellan gum composition with a denaturing agent prior to combination of the gum with milk. This method is the subject of U.S. Pat. No. 6,663,911.

Finally, US patent application publication 2005/0266138 discloses a method for preparation of a low calcium sensitive HA gellan gum, where a fermentation broth containing the gellan gum is adjusted to a pH about 7.5 followed by a subsequent step of pasteurization of the broth.

OBJECT OF THE INVENTION

It is an object of embodiments of the invention to provide alternative means and methods for preparation of gellan gum which is, e.g., in turn useful as a stabilizer in the food industry, namely for the production of dairy products and beverages.

The invention is particularly useful for dairy products with a desired long shelf life at room temperature or above, in that no off-taste is detected after a long storage time.

SUMMARY OF THE INVENTION

It has been found by the present inventor that the treatment of a gellan containing broth by a combination of a chelating agent and particular enzymes enables that no development of an off-taste is detected in milk product to which the gellan gum isolated from the broth has been added. It has also been found that a thermal treatment of the broth leads to the reduction of the development of off-taste. Performing both the 'chelatant-enzymes' treatment and the thermal treatment ensures exceptionally good results, even in cases where the gellan producing strain is not genetically modified.

For the good efficiency of the process:
The broth treated is kept warm/hot for the precipitation with alcohol, typically above the gelling temperature. The warm temperature leads the broth to behave like a liquid and not as a gel and allows an efficient mixing with the alcohol. Thus, it ensures a better quality of the precipitation and a better yield for the recovery of the fibres.
The precipitation is run continuously, mixing the flow of the broth with the flow of the alcohol, typically with the help of a pump. Then a residence time of some minutes allows the fibres to fully precipitate in the total flow. Doing so, compared with a batch process, the ratio of alcohol introduced is lower, typically 1/1 in weight, thus significantly reducing the costs of production.

So, in a first aspect the present invention relates to a method for the production of gellan gum, under mixing conditions, the method comprising
a) providing a fermentation broth or other liquid medium, which contains gellan gum, b) if necessary adjusting the temperature and the pH of the fermentation broth or liquid medium to allow enzymatic treatment in step c, c) adding one or more enzymes capable of reducing or abolishing the enzymatic activity of *S. elodea* derived arylsulfatase and/or β-glucuronidase, said one or more enzymes being added in an amount sufficient to reduce or abolish the enzymatic activity of *S. elodea* derived arylsulfatase and/or β-glucuronidase in the broth or liquid medium, and/or treating the broth/liquid medium at a temperature between 90° C. and 125° C. for a period of time sufficient to reduce or abolish the enzymatic activity of *S. elodea* derived arylsulfatase and/or β-glucuronidase in the broth/liquid medium, and d) optionally recovering the gellan gum from the gellan gum containing broth/liquid medium.

In a second aspect, the invention relates to preparation of a gellan containing food product or drug formulation, the method comprising admixing gellan gum obtained by the method of the first aspect of the present invention with food ingredients or drug components and subsequently effecting gelation of the gellan gum so as to obtain said gellan containing food product or drug formulation.

In a third aspect, the present invention relates to a food product or a drug formulation comprising as one ingredient, a gellan gum obtained by the method of first aspect of the present invention.

DETAILED DISCLOSURE OF THE INVENTION

Definitions

An "*S. elodea* derived arylsulfatase" is an arylsulfatase present in *S. elodea* or in other gellan gum producing *Sphingomonas* strains. An *S. elodea* derived arylsulfatase does hence not need to be produced by *S. elodea*, but rather by a strain which produces gellan gum. Arylsulfatases constitute a group of enzymes active in the hydrolysis of sulfates and the metabolism of mucopolysaccharides.

An "*S. elodea* derived β-glucorunidase" is a β-glucorunidase present in *S. elodea* or in other gellan gum producing *Sphingomonas* strains. An *S. elodea* derived β-glucorunidase does hence not need to be produced by *S. elodea*, but rather by a strain which produces gellan gum. β-glucorunidases are enzymes that attack terminal glycosidic linkages in natural and synthetic glucuronides.

A "food product" is a product intended for oral intake by humans as part of the daily diet. The term covers both solid, semi-solid and liquid products, in particular the products discussed above, i.e. the food products discussed in Duxbury, D D: "Multi-functional gum gets final FDA approval: gellan gum offers formulators low use levels and high versatility", Food Processing. Issue February 1993. Typical food products thus include bakery fillings, confections, dairy products, dessert gels, frostings, icings and glazes, jams and jellies, low-fat spreads, microwavable foods, puddings, sauces, structured foods, and toppings.

A "drug formulation" is a mixture between one or more pharmaceutically active ingredients and at least one carrier, vehicle or excipient—drug formulations of particular interest are according to the present invention those which are intended for oral intake such as gels and coated tablets and capsules.

"Dairy products" are defined as foodstuffs produced from milk coming from cows or other mammals.

"UHT milk" means milk treated at Ultra High Temperature, typically about 135-140° C., during a few seconds.

"HTST milk" means milk treated at High Temperature Short Time, that is to say about 70-75° C. for 15-30 seconds.

"Pasteurization" is defined as a moderate heat treatment not leading to sterilization. The treatment can be e.g. HTST or UHT.

"Diluted milk" means a whole milk diluted with water, lowering the final amount of proteins to 2% or 1%.

"GC" and "MS" and "SIM" means Gas Chromatography, Mass Spectroscopy, Selective Ion Monitoring, respectively.

A "chelating agent" is in the present context a substance capable of binding and stabilizing metallic ions by means of the formation of an inert complex compound or ion in which a metallic atom or ion is bound at two or more points to the substance so as to form a ring structure.

A "protease" (or "proteolytic enzyme) is an enzyme, which degrades proteins and polypeptides by breaking the peptide bonds in said proteins or enzymes. According to the present invention, suitable proteases are those capable of degrading *S. elodea* derived arylsulfatase and/or β-glucuronidase to such a degree that the enzymatic activity thereof is substantially reduced or abolished. Preferred proteases can be derived from any source and may be naturally occurring or may be synthetic, semi-synthetic or recombinant analogues of naturally occurring proteases.

"Lysozyme", also known as muramidase or N-acetylmuramide glycanhydrolase, denotes a family of enzymes (EC 3.2.1.17) which catalyze hydrolysis of 1,4-beta-linkages between N-acetylmuramic acid and N-acetyl-D-glucosamine residues in a peptidoglycan and between N-acetyl-D-glucosamine residues in chitodextrins.

Specific Embodiments of the Invention

First Aspect

In one embodiment of the first aspect of the invention relating to preparation of gellan gum, the mixing conditions may be provided by any means conventionally used in the art and are typically provided by a stirring power input and/or an aeration flow. Mixing may thus be accomplished by use of rotors, propellers, pumps, etc. but also by mechanical movement (e.g. via rolling or tipping) of the entire compartment where the broth is contained—the important goal to achieve is a satisfactory mixing of the contents in the gellan containing broth or liquid medium. Also, the air flow used to maintain a satisfactory aeration during the process may be used to provide the necessary mixing.

A chelating agent may advantageously be added to the broth/liquid medium in step a or in step b. Typically, the chelating agent is selected from citric acid, oxalic acid, phosphoric acid, DTPA, EDTA, and NTA. In the event the chelating agent is citric acid, it is preferably added in the form of an about 50% solution to the broth/liquid medium.

In one embodiment (when the method entails addition of enzymes in step c), the temperature is adjusted to between 20 and 80° C., such as between 50 and 60° C., preferably between 53 and 57° C. in step b). Typically, but not necessarily, the temperature is adjusted by direct injection of steam into a fermentation tank comprising the fermentation broth/liquid medium. It should be noted that the exact choice of temperature set point typically depends on the characteristics of the enzyme(s) being added—if, for instance, the enzymes exhibit maximum enzymatic activity at temperatures lower than 20 (if they e.g. have been isolated from organisms that live under cold or cool conditions), the temperature adjustment will obviously aim at reaching a temperature interval at which the enzymes perform satisfactorily.

In another embodiment, step b) further comprises an adjustment of pH. This is also of particular relevance when the method entails addition of enzymes in step c), so the pH is preferably adjusted to be in the range of the optimum activity of said one or more enzymes used in step c. Preferably, the adjustment of pH is done by addition of NaOH, but other alkaline substances may be utilised.

In a further embodiment, the addition of chelating agent and the adjustment of temperature in steps a) and b) are initiated substantially simultaneously.

The one or more enzymes added in step c) are preferably one or both of a lysozyme and a protease, such as alcalase.

In step c, the broth/liquid medium is preferably kept at a temperature about 55° C. at about pH 8 for a period of time followed by a subsequent adjustment of pH to between 6 and 7.5, preferably between 6.5 and 7. A temperature "about 55° C." is intended to denote a temperature not below 50° C. and not above 60° C. Normally the temperature will not be below 51° C., and it is preferred that the temperature is not below 52° C.; it is more preferred that the temperature is not below 53°, and it is especially preferred that it is not below 54° C. It is further preferred that the temperature does not exceed 59° C., and it is preferred that it does not exceed 58° C. It is more preferred that the temperature does not exceed 57°, and it is especially preferred that it does not exceed 56° C. The most preferred temperatures about 55° C. are in the range between 54.5 and 55.5°.

The thermal treatment in step c) is preferably performed at a temperature between 90 and 125° C., and preferably in the temperature range between 100 and 120° C. Preferred temperatures are thus about 100, 101, 102, 103, 104, 105, 106, 107, 108, 109, 110, 111, 112, 113, 114, 115, 116, 117, 118, 119 or 120° C.

In certain embodiments of the invention, step c) comprises both addition of the one or more enzymes as well as exercise of the thermal treatment. However, in other embodiments, step c) comprises addition of one or more enzymes but not thermal treatment, and in other embodiments step c) comprises thermal treatment but not enzyme treatment.

In embodiments where the broth/liquid medium is treated at a temperature between 90° C. and 125° C. in step c, the broth/liquid medium is preferably cooled down to a temperature which still exceeds the gelling temperature of the gellan gum (e.g. to about 80° C.) and then precipitated, e.g. by addition of an alcohol such as isopropanol. In preferred version of this embodiment the precipitation is a continuous precipitation.

In other, broadly defined embodiments of the first aspect, the invention generally relates to use of lysozyme and/or protease for reducing or abolishing the enzymatic activity of S. elodea derived arylsulfatase and/or β-glucuronidase in a gellan gum containing broth/liquid medium. Similarly, the use of elevated temperature for reducing or abolishing the enzymatic activity of S. elodea derived arylsulfatase and/or β-glucuronidase in a gellan gum containing broth/liquid medium also constitute an embodiment of the first aspect, as does use of a combination of a 1) lysozyme and/or protease and 2) elevated temperature for reducing or abolishing the enzymatic activity of S. elodea derived arylsulfatase and/or β-glucuronidase in a gellan gum containing broth/liquid medium.

These uses falling under the first aspect can also be regarded as use of elevated temperature and/or of lysozyme and/or of protease in gellan gum production to prevent subsequent off-taste in gellan containing products.

$2^{nd}$ Aspect

When using the gellan gum obtained by the method of the first aspect of the present invention, the gellan gum is generally employed in a manner known per se. That is, the gellan gum is admixed with the other ingredients of the product to be produced using process parameters identical to or equivalent to those utilised when using gellan gum obtained by methods known in the art. The method of the second aspect does hence not produce a product which has different characteristics in terms of structural differences but rather in a product which exhibits a considerable longer shelf-life before any undesirable off-taste develops due to the activity of S. elodea arylsulfatase and/or β-glucuronidase activity.

Hence, in order to exercise the $2^{nd}$ aspect of the invention, the skilled person may e.g. utilise the guidelines and recommendations provided in Duxbury et al. (supra); Giavasis I, Harvey L M, McNeil B : "Gellan Gum," Crit Rev Biotechnol, 20(3),177-211,2000; Miyazaki S, Aoyama H, Kawasaki N, et al.: "In situ gelling formulations as Gellan vehicles for oral delivery [J], " J Controlled Release, 60 (3), 287, 1999; Morris V J: "*Bacterial polysaccharides,* in Food polysaccharides and their application", Stephen A M, Editor, Marcel Dekker, New York, 341-375, 1995.

$3^{rd}$ Aspect

Closely related to the above aspects is the $3^{rd}$ aspect, which relates to products (food products or drug formulations) containing the gellan gum obtained by the method of the invention.

Food products which contain the gellan gums are typically selected from the group consisting of bakery fillings, confections, dairy products, dessert gels, frostings, icings and glazes, jams and jellies, low-fat spreads, microwavable foods, puddings, sauces, structured foods, and toppings, whereas drug formulations typically are selected from the group consisting of a gel, a tablet, and a capsule. In both cases, the gellan gum obtained by the method of the invention is preferably present in an amount effective to function as a thickener and/or emulsifier and/or stabiliser.

EXAMPLES

Materials and Methods

1. 'Chelatant-Protease' Treatment Protocol

During the fermentation, the pH is adjusted between 6.4 and 7 depending on the metabolism. When fermentation is completed and because there is no more sugar to metabolize, the respiratory activity decreases and the pH, which is no longer controlled, increases (because of the release of dissolved $CO_2$).

Then the treatment, under mixing conditions, is:
The broth is heated by a direct injection of steam in the fermenter until about 55° C. is reached and air is fed at the same time to help mix.
As soon as the heating is started, 160 kg of a 50% solution of citric acid is added with help of a pump. The pH should drop to about 5.
Heating is stopped when T=55° C.
Once the temperature has reached 55° C., the pH is increased to about 8.0 with a base.
The pH is kept at about 8.0.
The following enzymes are added:
  Lysozyme at about 230 ppm
  Protease at about 1000 ppm
The mixture is kept at about 55° C. for about 1 hour while the pH is maintained at about 8.0.
The pH is then lowered to about 7 using, e.g., $H_2SO_4$.
The broth is transferred to a holding tank while adding 10% of isopropanol.

Mixing conditions are adjusted by the stirring power input and/or aeration flow.

A number of experiments where performed with different proteases and with modified versions of the 'chelatant-protease' treatment:

Experiments 56-6 and 58-B: the protocol conditions, but Protease was type I (Alcalase 2.4 L) at 500 ppm.

Experiment 72-3: the protocol conditions but with Protease type II (Protex 6L).

Experiments 72-4 and 72-7: the protocol conditions, but with Protease type III (Proteinase T) at 2000 ppm.

Experiment 72-5: the protocol conditions, but with Protease type IV (Multifect) at 2000 ppm.

Experiments 72-6: the protocol conditions, but Protease was type I (Alcalase 2.4 L) at 1000 ppm.

Experiments 74-2 and 80-A: the protocol conditions with Protease type II (Protex 6L).

Experiment 80-B: the protocol conditions, but with sodium citrate instead of citric acid and no pH control.

2. Thermal Treatment Protocol

Following the Chelatant-protease treatment, the broth undergoes heat treatment as follows:

The pH is adjusted between 6 and 7.5, and preferably at 6.5.

The temperature is adjusted between 90° C. and 125° C., preferably between 100-110° C.

The residence time is at least 15 minutes.

In the following experiments, the conditions applied are as follow:

Experiment 72-1: 100° C., pH=7, residence time 15 min.
Experiment 72-2: 120° C., pH=7, residence time 20 min.
Experiments 74-2 and 74-3: 100° C., pH=6.5, residence time 20 min.
Experiments 72-3, 72-4, 80-A, 80-B: 100° C., pH=6.5, residence time 15 min.

After the thermal treatment, the broth is cooled down to a temperature not lower than the gelling temperature, e.g. at about 80° C. Then it is precipitated in a continuous process, by addition of isopropanol.

3. NaOH Treatment Protocol

U.S. Pat. No. 6,663,911 describes different protocols using an alkali or an oxidising agent to treat a gellan broth.

In order to compare our invention to the one described in the U.S. Pat. No. 6,663,911, we applied the protocols described in the U.S. Pat. No. 6,663,911 to our own broth. The conditions are as follows:

Experiments 56-8, 72-8, and 74-3: 1 g NaOH/10 liters of broth, 50° C., 3 h, pH not controlled.

Experiments 56-9: NaOH added up to increase the pH=9 (about 2 g/10 liters of broth), then, 50° C., 3 h, pH not controlled.

4. NaOCl Treatment Protocol

U.S. Pat. No. 6,663,911 describes different protocols using an alkali or an oxidising agent to treat a gellan broth.

In order to compare our invention to the one described in the U.S. Pat. No. 6,663,911, we applied the protocols described in the U.S. Pat. No. 6,663,911 to our own broth. The conditions are as follow:

Experiments 56-7, and 72-10: 1000 ppm NaOCl, 50° C., 3 h, pH not controlled.

5. Preparation of Samples in UHT Milk

Trials in UHT milk have to be run to determine if the final gellan product is suitable for an application in milk.

A gellan gum known in the market such as KELCOGEL LT100 from CP-Kelco, was used as a positive control, in the following protocol.

Ingredients in %:
Cream 35% fat: 8.45
Saccharose: 5
Gellan gum: 0.09 to 0.15
Skimmed milk (pasteurised): 86.4 to 86.46
Protocol for UHT Plates Heat Exchanger:
Blend all ingredients.
Preheating at 70° C.
Homogenize in 2 steps up to 100 bar at 70° C.
Heating at 90° C./holding time 30 s.
UHT treatment at 140° C. for 3 seconds.
Cooling down to 10° C. and fill in the containers
Storage at two different temperatures: 5° C. and 20° C.

6. Assays for Determination of Para-cresol Content p-Cresol concentrations have been determined by Gas Chromatography:

To 10 g of sample add 1 ml 2N HCl, 5 ml demineralised water and internal standard corresponding to approx. 100 ppb. The internal standard is ethyl anisate.

Extract with 10 ml diethylether using magnetic stirring for 30 minutes.

The ether extract is analysed by GC/MS/SIM.

Each sample is analysed in duplicate and standard addition of p-cresol at a level of 50 and 100 ppb is performed to several samples to verify method performance.

Calibration is performed in the range 5 to 250 ppb (external calibration in diethyl ether).

Results

1. Evaluation of Series 1 After a 4-week Storage.

Storage at 4° C.:

| | | |
|---|---|---|
| Exp. 56-4 (no treatments): | off-taste | 55 ppb of p-cresol |
| Exp. 56-6 (Chelatant/protease): | no off-taste | 12 ppb of p-cresol |
| Exp. 56-7 (NaOCl 1000 ppm): | bitter off-taste | |
| Exp. 56-8 (NaOH 1 g/kg): | bitter off-taste | |
| Exp. 56-9 (NaOH for pH = 9): | slight off-taste | |

Storage at 20° C.:

| | | |
|---|---|---|
| Exp. 56-6 ('Chelatant/protease): | no off-taste | 9 ppb of p-cresol |
| Exp. 56-7 (NaOCl 1000 ppm): | hot milk taste | |
| Exp. 56-8 (NaOH 1 g/kg): | off-taste | |
| Exp. 56-9 (NaOH for pH = 9): | fermented milk taste | |

Positive Control

| | | |
|---|---|---|
| At 20° C.: | strong cow-like off taste | 160 ppb of p-cresol |
| At 4° C.: | cow-like off taste | 85 ppb of p-cresol |

2. Evaluation of Series 2 After a 4-week Storage

Storage at 20° C.:

| | |
|---|---|
| Exp. 58-A (no treatment): | off-taste |
| Exp. 58-B (Chelatant/proteasel): | milky, no off-taste |

Positive Control Strong Cowy Off-taste, Bitterness

3. Evaluation of Series 3 After a Storage Time Up to 16 Weeks

For the following experiments, differents protocols have been applied.

Exp. 72-1 (thermal treatment at 100° C., 15 min)
Exp. 72-2 (thermal treatment at 120° C., 20 min)
Exp. 72-3 (Chelatant/protease treatment+thermal treatment at 100° C., 15 min)

Exp. 72-4 (Chelatant/protease treatment+thermal treatment at 100° C., 15 min)
Exp. 72-5 (Chelatant/protease treatment)
Exp. 72-6 (Chelatant/protease treatment)
Exp. 72-7 (Chelatant/protease treatment)
Exp. 72-8 (NaOH, 1 g/l, at 50° C.)
Exp. 72-10 (NaOCl, 1000 ppm, at 50° C.)
Exp. 74-2 (Chelatant/protease treatment+thermal treatment at 100° C., 20 min)
Exp. 74-3 (NaOH+thermal treatment at 100° C., 20 min)
Exp. 80-A (Chelatant/protease treatment+thermal treatment at 100° C., 15 min)
Exp. 80-B (Chelatant/protease treatment, replacing citric acid by sodium citrate, no pH control+thermal treatment at 100° C., 15 min)
Exp. 1201, Exp. 1202, Exp. 1301, Exp. 1401, Exp. 1402
For all the previous 5 experiments, at industrial scale, we applied 'Chelatant/protease' treatment+thermal treatment at 100° C., 20 min.

Evaluations for the off-taste for the series 3 are shown in the following Table:

Storage at 20° C.

| Reference | Dosage* (%) | Evaluation of off-taste after # of weeks: 4 | 8 | 16 | p-cresol (ppb) |
|---|---|---|---|---|---|
| 72-1 | 0.15 | barn-like– | — | — | — |
| 72-2 | 0.15 | no | no | — | 18 |
| 72-3 | 0.15 | no | no | no | 16 |
| 72-4 | 0.09 | no | no | no | <10 |
| 72-5 | 0.15 | no | no | — | — |
| 72-6 | 0.11 | no | no | no | <10 |
| 72-7 | 0.14 | no | no | no | <10 |
| 72-8 | 0.15 | barn-like | barn-like | — | — |
| 72-10 | 0.13 | no | off-taste | barn-like– | — |
| positive control | 0.15 | barn-like+ | barn-like++ | barn-like+++ | 90 |
| Milk (negative control) | — | no | no | no | — |
| 74-2 | 0.12 | no | no | no | <10 |
| 74-3 | 0.15 | no | off-taste but no p-cresol | off-taste but no p-cresol | <10 |
| positive control | 0.15 | barn-like | barn-like+ | barn-like++ | 60 |
| Milk (negative control) | — | no | no | no | — |
| 80-A | 0.15 | no | no | no | <10 |
| 80-B | 0.15 | no | no | no | 14 |
| positive control | 0.15 | barn-like+ | barn-like++ | barn-like+++ | 100 |
| Milk | — | no | no | no | — |
| 1201 | 0.15 | no | no | no | <10 |
| 1202 | 0.15 | no | no | no | <10 |
| 1301 | 0.15 | no | no | no | <10 |
| 1401 | 0.15 | no | no | no | <10 |
| 1402 | 0.15 | no | no | no | <10 |
| positive control | 0.15 | barn-like | barn-like+ | barn-like++ | 80 |
| Milk (negative control) | — | no | no | no | — |

*Dosage is the amount of gellan gum in the milk.
For the evaluation, + means 'detected', ++ means 'significant', +++ means 'strong'.

Discussion

It is confirmed that the 'chelatant/protease' protocol alone or in addition with a thermal treatment leads to very good results.

The protocols with NaOH or NaOCl disclosed in U.S. Pat. No. 6,663,911 can lead to an off-taste; this off-taste is different from the off-taste characterising the presence of p-cresol.

Concerning the thermal treatment as sole treatment, it seems that the temperature is a sensitive parameter. Two trials support this point:
Exp. 72-1 with 100° C. led to a p-cresol off-taste.
Exp. 72-2 with 120° C. led to no p-cresol off-taste.

A pasteurization (understood in the state of the art as being performed at a moderate temperature and/or duration) would therefore seem to be insufficient to denature the p-cresol causing enzymes.

It is therefore preferable to use a thermal treatment, with temperature above 100° C. and a long duration of about 15 minutes.

Also, in addition to the trials described above, a trial has been run in retorted milk, which means "99.78% milk+0.2% sucrose+0.02% gellan gum" sterilized in cans at 121° C. for 15 min, in an autoclave. No p-cresol is detected after 6-weeks of storage at either 20° C. or 40° C.

In the enzymatic reaction releasing p-cresol, because the positive control leads to a quite high concentration in p-cresol, this indicates that there is no limitation by the precursors present in the milk. Thus, it can be assumed that the enzymes are the limiting factor. So, the production of p-cresol will directly depend on the percentage of gellan in the milk. A test run at 0.15% can be considered as an accelerated test of a final 0.05% recipe.

If no p-cresol detected after 16 weeks with a 0.15% dosage, it can be assumed that no p-cresol would be detected after 48 weeks with a 0.05% dosage.

CONCLUSIONS

There is no doubt that a 'chelatant/protease' treatment applied to the gellan broth results in no development of a p-cresol off-taste in UHT milk during a long storage duration.

Following some trials and also considering the results in retorted milk, we can conclude that a thermal treatment is also able to denature the enzymes responsible of the p-cresol production.

Therefore, both these approaches in isolation are useful according to the invention for reducing/abolishing off-taste problems in gellan gum containing products. However, it appears that optimum results are obtained when combining a "chelatant/protease" treatment in combination with a thermal treatment.

The invention claimed is:

1. A method for a production of gellan gum, under mixing conditions, comprising:
providing a liquid medium containing the gellan gum, wherein the gellan gum comprises one or more of a *S. elodea* derived arylsulfatase or a β-glucuronidase;
adjusting a temperature of the liquid medium to facilitate enzymatic treatment;
adjusting a pH of the liquid medium to about 8.0 to facilitate the enzymatic treatment;
applying an enzymatic treatment to the liquid medium, wherein the enzymatic treatment comprises adding a protease capable of reducing or abolishing the enzymatic activity of one or more of *S. elodea* derived arylsulfatase or β-glucuronidase, wherein the protease is added in an amount sufficient to reduce or abolish the enzymatic activity of the one or more of the *S. elodea* derived arylsulfatase or the β-glucuronidase in the liquid medium, and wherein no lysozyme is added to the liquid medium;
treating the liquid medium at a temperature of between 100° C. and 125° C. for a period of time sufficient to reduce or abolish enzymatic activity of the one or more of the *S. elodea* derived arylsulfatase or the β-glucuronidase to reduce or abolish an off-taste of a product to which the gellan gum is added; and recovering the gellan gum from the liquid medium; and wherein no oxidative agent is added to the liquid medium, and wherein a chelating agent is added to the liquid medium before the enzymatic treatment is applied to the liquid medium.

2. The method of claim 1, wherein the enzymatic treatment comprises adding an alcalase that confers protease enzymatic activity.

3. The method of claim 2, wherein the liquid medium is treated at the temperature between 100° C. and 120° C.

4. The method of claim 1, wherein the liquid medium is treated at the temperature between 100° C. and 120° C.

5. The method of claim 1, wherein the recovered gellan gum is admixed with food ingredients to effect gelation of the gellan gum to produce a gellan-containing food.

6. The method of claim 5, wherein the gellan-containing food comprises bakery fillings, confections, dairy products, dessert gels, frostings, icings, glazes, jams, jellies, low-fat spreads, microwavable foods, puddings, sauces, structured foods, and toppings.

7. The method of claim 1, wherein the recovered gellan gum is admixed with drug components to effect gelation of the gellan gum to produce a gellan-containing drug composition suitable for oral use.

8. The method of claim 7, wherein the drug composition is selected from the group consisting of a gel, a tablet, and a capsule.

9. The method according to claim 1, wherein the chelating agent is selected from the group consisting of citric acid, oxalic acid, phosphoric acid, DTPA, EDTA, and NTA.

10. The method according to claim 1, wherein the chelating agent is citric acid.

* * * * *